United States Patent [19]

Walther et al.

[11] Patent Number: 5,173,509

[45] Date of Patent: Dec. 22, 1992

[54] SURAMIN AND ACTIVE ANALOGUES THEREOF IN THE TREATMENT OF HYPERCALCEMIA

[75] Inventors: McClellan M. Walther, Gaithersburg, Md.; Renato V. LaRocca, Sterling, Va.; Charles E. Myers, Bethesda, Md.; Cy A. Stein, North Potomac, Md.; W. Marston Linehan, Rockville, Md.

[73] Assignee: The United States of America as represented by the Department of Health and Human Services, Washington, D.C.

[21] Appl. No.: 500,913

[22] Filed: Mar. 29, 1990

[51] Int. Cl.$^5$ .............................................. A61K 31/17
[52] U.S. Cl. ..................................................... 514/597
[58] Field of Search ......................................... 514/597

[56] References Cited

PUBLICATIONS

H. Connerty et al., The American Journal of Clinical Pathology, vol. 45, No. 3 pp. 290–296 (Jun. 1965).
R. Klecker et al., Journal of Liquid Chromatography, 8(9), 1685–1696 (1985).
Stein et al., Journal of Clinical Oncology, vol. 7, No. 4 (Apr. 1989) pp. 499–508.
Jentsch et al., J. of Gen. Virol. (1987), vol. 68, pp. 2183–2192.

*Primary Examiner*—Jerome D. Goldberg
*Attorney, Agent, or Firm*—Birch, Stewart, Kolasch & Birch

[57] ABSTRACT

A method is disclosed for the treatment of hypercalcemia in a patient, by administering to the patient an effective amount of suramin, or an active analogue thereof, for lowering calcium plasma levels in the patient. Human data shows a single course of treatment lowers plasma calcium levels to normal for three months.

3 Claims, 2 Drawing Sheets

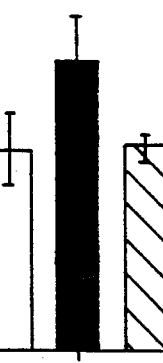
FIG. IA
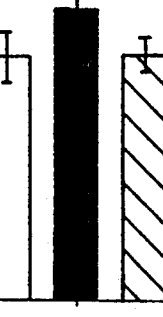
FIG. IB

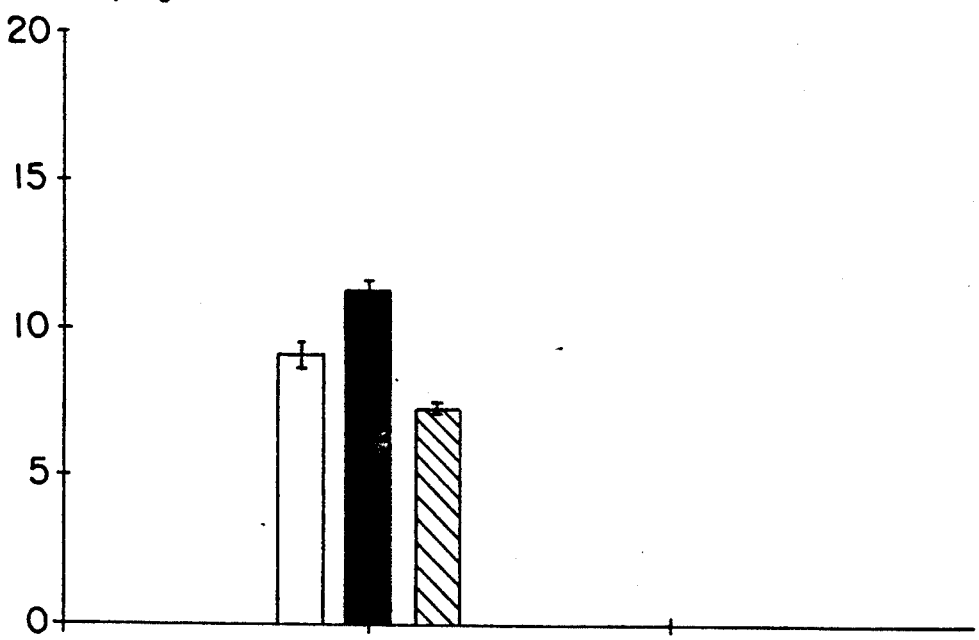
FIG. IC

SURAMIN AND ACTIVE ANALOGUES THEREOF IN THE TREATMENT OF HYPERCALCEMIA

FIELD OF THE INVENTION

The present invention is concerned with the use of suramin and active related compounds thereto, in methods of treating hypercalcemia.

BACKGROUND OF THE INVENTION

Hypercalcemia can occur as a result of numerous different clinical conditions, wherein there are produced high concentrations of free calcium ions in the circulating blood. Causes of hypercalcemia can include for example, hyperparathyroidism, cancer (with or without bone metastasis), hypervitaminosis D, sarcoidosis, thyrotoxicosis, immobility and adrenal insufficiency, among others.

Present treatments for hypercalcemia include vigorous intravenous hydration with diuresis to purge calcium from a patient's body. Furthermore, glucocorticoids are also occasionally used in conjunction with such intravenous hydration techniques to lower serum calcium levels. Other methods, which have been utilized to treat hypercalcemia, include administering Mitomycin (a chemotherapeutic agent directly toxic to tumor cells and which can decrease plasma calcium levels), administering calcitonin (a thyroid hormone which can inhibit bone resorption and thus decrease plasma calcium levels), Etidronate (a chemical compound which binds to calcium phosphate surfaces and inhibits crystal resorption of bone) and administering phosphate. Treatment results with each of the above discussed methods are relatively short lived, and as a consequence, hypercalcemia often readily returns after each of the above discussed treatments are discontinued.

Suramin was used by Stein et al in clinical trials to treat patients with adrenalcortical carcinoma, renal cell carcinoma and leukemia/lymphoma (*J. of Clinical Oncology*, Vol. 7, pp. 499–508, 1989). Stein et al reported that they treated a patient with cancer metastatic to bone and with hypercalcemia refractory to calcitonin. The patients' hypercalcemia normalized for three months after initiation of suramin therapy in the setting of disease stabilization radiographically. *J. of Clinical Oncology*, Vol. 7, pp. 499–508 (1989) is incorporated herein by reference.

Stein et al, in U.S. patent application, Ser. No. 07/321,055, filed on Mar. 9, 1989, disclose a general method for treating cancer in a patient by administering suramin sodium to a patient so that suramin serum (plasma) levels are maintained between about 50–300 mcg/ml. U.S. patent application Ser. No. 07/321,055 of Stein et al is incorporated herein by reference.

Jentsch et al in *J. Gen. Virol.*, Vol. 68, pp. 2183–2192 (1987) tested 90 analogues of suramin for their ability to inhibit the exogenous reverse transcriptase (RT) of human immuno-deficiency virus type I (HIV-I). Of the compounds tested, 57 suramin analogues inhibited poly (rC)oligo (dG) dependent RT activity. The Jentsch et al reference is incorporated herein by reference, as are the structures of the 90 suramin analogues disclosed therein.

SUMMARY OF THE INVENTION

One object of the present invention is to provide an advantageous method for the treatment of hypercalcemia, wherein more than short lived effectiveness in treating hypercalcemia is achieved. Another object of the present invention is to provide an advantageous method for treating hypercalcemia, so that the occurrence of arrhythmias, altered renal functions and mental states, and the like, which can result from hypercalcemia are lessened and/or prevented. Such objectives, among others, are achieved with the following inventive methods.

Methods are provided herein for treating hypercalcemia in a patient, wherein there is administered to a patient in need thereof, an effective amount of suramin, or a pharmaceutically acceptable salt thereof, for the treatment of hypercalcemia. Such administration is contemplated to include intravenous, intramuscular or subcutaneous administration, with the preferred routes of administration being bolus intravenous or continuous intravenous infusion. In any event, pharmaceutically acceptable carriers for the pharmaceutically active compounds are thought most desirable to aid in the administration of the active compounds.

In the methods of the present invention, it is thought that plasma levels, of the active compounds of the present invention, being greater than about 300–350 mcg/ml should be avoided, since toxic effects of the active compounds herein encompassed are produced at such high plasma concentrations. However, the compounds herein encompassed are most effective in treating hypercalcemia below these high plasma concentrations, and this limitation should not be deemed to detract from the efficacious methods herein encompassed.

With regard to a lower limit on an effective amount of the compounds herein taught for treating hypercalcemia, it is generally thought that plasma concentrations of greater than about 50 mcg/ml should be achieved. Since the half life of the active compounds herein encompassed is relatively long (suramin's half life in humans is about 44 54 days), it is envisioned that plasma levels of greater than 50 mcg/ml can be maintained for lengthy periods of time, once an effective concentration level of the active compounds herein encompassed is achieved. In order to aid those desiring to practice the present invention, the following glossary of terms is provided herein to remove any ambiguity which may exist to their meanings as used herein.

The term "suramin" as used herein means the commercially available compound 8,8'-[carbonylbis[imino-3,1-phenylenecarbonylimino(4-methyl-3,1-phenylene)carbonylimino]]bis-1,3,5-naphthalenetrisulfonic acid. A method for its preparation can be found in Great Britain Patent 224,849 (1929). The compound's disclosed therapeutic categories, include utility as an anti-cancer agent, an HIV inhibitor, as an antitrypanosomal and antifilarial agent.

The term "suramin sodium" as used herein refers to the hexasodium salt of suramin.

The term "active suramin analogue" as used herein refers to suramin analogues disclosed by Jentsch et al in *J. Gen. Virol.*, Vol. 68, pp. 2183–2192 (1987), which are effective in inhibiting or reducing hypercalcemia, and pharmaceutically acceptable salts thereof. Such active suramin analogues would include the preferred 57 suramin analogues listed in Tables 3 and 4 of the Jentsch et al reference.

The term "suramin analogue" as used herein, refers to any compounds having the sequence of elements of Table 1 of the Jentsch et al reference, whereby the elements are selected from the group consisting of the composition moieties of Table 2 in Jentsch et al. All of these compounds are incorporated herein by reference.

The term "plasma" as used herein refers to whole blood plasma having cell bodies spun out by centrifugation, or similar method. Exemplary of suitable methods which may be utilized to obtain plasma, and furthermore to quantify suramin or suramin analogue concentration levels therein, is that of R. Klecker and J. Collins, *J. Lig. Chromatog.*, Vol. 8, pp. 1685-1696 (1985), hereby incorporated by reference.

The term "plasma calcium level" as used herein, means the level of calcium ions found in the plasma of human patients, and includes calcium which is bonded to proteins and is non-diffusible, as well as calcium which is diffusible and exists in a free ionized form as well as in a complexed form. A suitable method of determining calcium plasma levels is disclosed by Connerty, H.V. and Briggs, A.R., *American Journal of Clinical Pathology*, Vol. 45, p 290 (1986).

The term "pharmaceutically acceptable carrier" as used herein, means any carrier suitable for use in an injectable composition which is acceptable for parenteral administration and is compatible with the active compound administered. Exemplary of such carriers are purified water USP, Arachis oil, buffered saline, and the like.

The term "pharmaceutically acceptable salt" as used herein, includes appropriate addition salts, alkali metal salts (sodium, potassium, etc.), hydrates, alcolates, quaternary salts, and the like of the active compounds herein encompassed, which salts are physiologically compatible in man.

BRIEF DESCRIPTION OF THE DRAWINGS

The present invention will become more fully understood from the detailed description given here and below and the accompanying drawings which are given by way of illustration only, and thus, are not limitative of the present invention, and wherein:

FIG. 1A. Graph of test results obtained in Example 1.
FIG. 1B. Graph of test results obtained in Example 2.
FIG. 1C. Graph of test results obtained in Example 3.

DETAILED DESCRIPTION OF THE INVENTION

The following detailed description of the present invention is provided as an aid to those desiring to practice the present invention. This description includes discussions relating to the present inventive methods and contains experimental testing examples, evidencing the efficacious properties of suramin and the active suramin analogues herein encompassed, which make them useful in the present inventive methods. There are also discussed pharmaceutical compositions which may be utilized to administer the active compounds of the present invention as well as their pharmaceutically acceptable salts. It is noted that the present description is not to be construed as limiting to the present invention or to the scope of protection afforded the present inventors therein, as the present discussions and examples presented herein are only meant to exemplify the present inventors' board inventive discovery.

The present inventors have discovered fortuitously that suramin, and active related analogues thereto, possess the ability to lower plasma levels of calcium, and more specifically, to lower the plasma levels of free calcium ion, in patients having elevated plasma calcium levels.

As noted above, the suramin analogues encompassed hereby include those analogues disclosed by Jentsch et al in J. Gen. Virol., vol. 68, pp. 2183-2192 (1987). In this regard, Jentsch et al disclose the structure of suramin and related analogues thereof in a manner similar to the following.

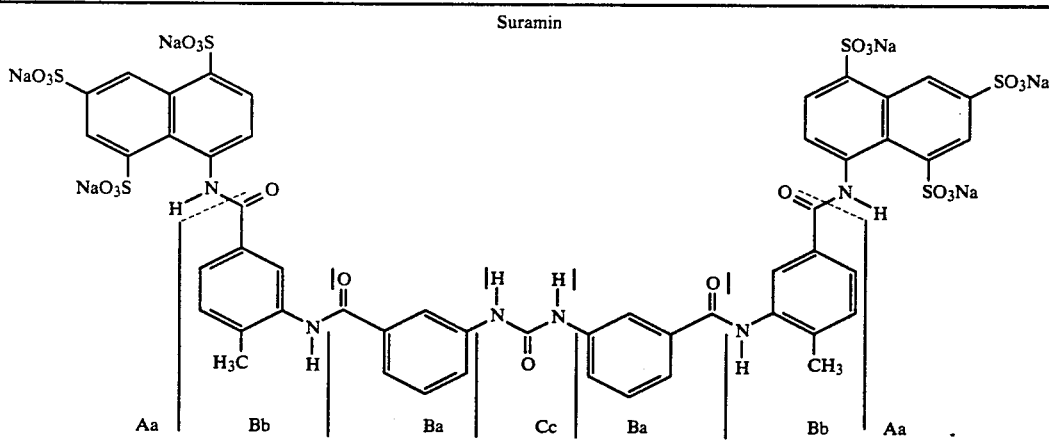

| Structural group | Sequence of elements* |
|---|---|
| (1) | A—B—B—C—B—B—A |
| (2) | A—B—C—B—A |
| (3) | A—B—B—C |
| (4) | A—B—C |

*Highly acidic group (A), aminobenzoyl group (B) and central group (C) are the structural elements of the compounds: (1) and (2) are symmetrical molecules; (3) and (4) are non-symmetrical molecules, precursors in the synthesis of (1) and (2), respectively.

Chemical composition of the structural elements A, B and C.

| Element | Chemical composition | Element | Chemical composition |
|---|---|---|---|
| Aa | 1-Aminonaphthalene-4,6,8-tri- | Bj | 3-C-2,4,6-trimethylbenzoyl |

-continued

Chemical Structure of Suramin, Its Analogues and Their Structural Elements

| | | | |
|---|---|---|---|
| | sulphonic acid | Bk | 4-C-benzoyl |
| Ab | 1-Aminonapthalene-3,6,8-tri-sulphonic acid | Bl | 4-C-3-methylbenzoyl |
| | | Bm | 2-(4-C-phenyl)benzoyl |
| Ac | Aniline-3-sulphonic acid | Bn | 3-(2-C-phenyl)benzyl |
| Ad | Aniline-4-sulphonic acid | Bo | 3(3-C-phenyl)benzoyl |
| Ae | Aniline-2,4-disulphonic acid | Bp | 3-(4-C-phenyl)benzoyl |
| Af | Aniline-2,5-disulphonic acid | Bq | 4-(2-C-phenyl)benzoyl |
| Ag | Ethylamine-2-sulphonic acid | Br | 4-(3-C-phenyl)benzoyl |
| Ah | Aniline-3-phosphonic acid | Bs | 4-(4-C-phenyl)benzoyl |
| Ai | Aniline-4-phosphonic acid | | |
| Aj | 4-Methylaniline-3-phosphonic acid | Ca | $-NO_2$ |
| Ak | $-NH-1,4-C_6H_4-(C(NH_2)(PO_3H_2)_2)$ | Cb | $-NH_2$ |
| Al | Ethylamine-2-phosphonic acid | Cct | $-NH-CO-NH-$ |
| | | Cd | $-NH-CS-NH-$ |
| Ba | 3-C-benzoyl* | Ce | $-NH-CO-1,4$-piperazino-$CO-NH-$ |
| Bb | 3-C-4-methylbenzoyl | Cf | $-NH-CO-1,4-C_6H_4-CO-NH-$ |
| Bc | 3-C-4-ethylbenzoyl | Cg | $-NH-CO-1,3-C_6H_4-CO-NH-$ |
| Bd | 3-C-4-i-propylbenzoyl | Ch | $-NH-CO-1,3-(5-NO_2-C_5H_3)-CO-NH-$ |
| Be | 3-C-4-t-butylbenzoyl | Ci** | $-NH-CO-1,3-(5-NH_2-C_6H_3)-CO-NH-$ |
| Bf | 3-C-4-phenylbenzoyl | Cj*** | $(3,5$-bis$(-NH-CO-)-C_6H_3-NH-)_2CO$ |
| Bg | 3-C-4-fluorobenzoyl | Ck | $-NH-CO$-4-methylpiperazino |
| Bh | 3-C-4-methoxymethylbenzoyl | Cl | $-NH-(7$-chloro-4-quinolinyl) |
| Bi | 3-C-2-methylbenzoyl | Cm | $-NH-CO-(5$-nitro-2-furyl) |

*C is $-N-H-$ for the benzoyl residues B adjacent to group A in compounds of type (1) and (3) above, in all others cases the central unit C.
**Compounds with central units Cc to Ci are symmetrical molecules with two identical residues attached to C.
***In compounds with the central unit Cj four identical residues are attached to Cj.

Additionally, the specific active suramin related analogues encompassed hereby, and disclosed by Jentsch et al, ibid, in Tables 3 and 4 thereof at pages 2187 and 2188 have the following structures and molecular weights as shown in Table 1.

TABLE 1

| Compound No. | Structure[1] | Molecular Weight[2] |
|---|---|---|
| 1[3] | (Aa-Bb-Ba-)$_2$Cc | 1429.2 |
| 2 | (Ai-Ba-)$_2$Cc | 698.4 |
| 3 | (Ab-Bk-Bk-)$_2$Cc | 1401.1 |
| 4 | (Aa-Ba-Ba-)$_2$Cc | 1401.1 |
| 5 | (Aa-)$_4$Cj | 1096.2 |
| 6 | (Aa-Bg-)$_2$Cc | 1198.2 |
| 7 | (Aa-Bi-Ba-)$_2$Cc | 1429.2 |
| 8 | (Aa-Bn-)$_2$Cc | 1315.1 |
| 9 | (Ab-Bk-Ba-)$_2$Cc | 718.6 |
| 10 | (Aa-Bc-)$_2$Cc | 1219.0 |
| 11 | (Aa-Bb-)$_2$Cg | 1295.1 |
| 12 | (Aa-Bb-Ba-)$_2$Cf | 1535.5 |
| 13 | (Aa-Bb-)$_2$Cc | 1191.0 |
| 14 | (Aa-Bs-)$_2$Cc | 1315.1 |
| 15 | (Ab-)Cl | 610.5 |
| 16 | (Ab-Bk-Ba-)$_2$Cc | 1401.1 |
| 17 | (Ah-Bk-)$_2$Cc | 654.4 |
| 18 | (Aa-Bc-Ba-)$_2$Cc | 1457.9 |
| 19 | (Aa-Bi-)$_2$Cc | 1191.0 |
| 20 | (Aa-Ba-)$_2$Cc | 1162.0 |
| 21 | (Ai-Bk-)$_2$Cc | 698.4 |
| 22 | (Aa-)Cl | 610.5 |
| 23 | (Aa-Bb-Ba-)$_2$Cg | 1535.3 |
| 24 | (Af-Bb-Ba-)$_2$Cc | 674.6 |
| 25 | Aa-Bs-Ca | 1060.9 |
| 26 | Ab-Bk-Bk-Ca | 717.6 |
| 27 | (Ae-Bb-Ba-)$_2$Cc | 1060.9 |
| 28 | (Ah-Ba-)$_2$Cc | 654.5 |
| 29 | Ab-Bk-Bk-Ca | 687.6 |
| 30 | Aa-Bs-Cb | 644.5 |
| 31 | Aa-Bb-Cl | 730.5 |
| 32 | (Ac-Bb-Ba-)$_2$Ce | 920.9 |
| 33 | (Aa-Ba-Bb-)$_2$Cc | 1429.2 |
| 34 | (Aa-Bd-)$_2$Cc | 1247.1 |
| 35 | (Aa-Bd-Bd-Bd-)$_2$Cc | 1723.6 |
| 36 | (Aa-Bh-Ba-)$_2$Cc | 1489.3 |
| 37 | (Aa-Bb-Bb-)$_2$Cc | 1457.3 |
| 38 | (Aa-Bb-)$_2$Cc | 1301.1 |
| 39 | (Aa-Bb-)$_2$Ce | 1485.4 |
| 40 | (Aa-Bj-Ba-)$_2$Cc | 1162.8 |
| 41 | (Ab-Bk-)$_2$Cc | 1429.2 |
| 42 | (Aa-Bl-Ba-)$_2$Cc | 1251.0 |
| 43 | (Aa-Bh-)$_2$Cc | 1191.0 |
| 44 | (Aa-Br-)$_2$Cc | 1351.1 |
| 45 | (Aa-Bg-Ba-)$_2$Cc | 1477.1 |
| 46 | (Aa-Bb-)Cm | 721.6 |
| 47 | (Aa-Bq-) | 1351.1 |
| 48 | (Aa-Bc-)$_2$Cc | 1275.1 |
| 49 | (Aa-Bm-)$_2$Cc | 1315.1 |
| 50 | (Aa-Be-Ba-)$_2$Cc | 1513.4 |
| 51 | (Aa-Bd-Ba-)$_2$Cc | 1485.4 |
| 52 | (Aa-Bf-)$_2$Cc | 1315.1 |
| 53 | (Aa-Bf-Ba-)$_2$Cc | 1553.4 |
| 54 | (Aa-Bj-)$_2$Cc | 1245.0 |
| 55 | (Aa-)Cm | 588.2 |
| 56 | (Ai-Bk-)$_2$Cd | 714.5 |
| 57 | (Ah-Ba-)$_2$Cd | 670.7 |

[1]Synthesis of each of the suramin analogues (compound numbers 2-57) have been previously reported (P. Nickel et al, (Arzneimittel-Forschung, Vol, 36, pp. 1153-57 (1986); and G. Holzmann et al, Biomedical Mass Spectrophotometry, Vol. 12, pp. 659-663 (1985)). A, B and C structural units are as defined above.
[2]Molecular weight of the sodium salt.
[3]Suramin (sodium salt).

Plasma calcium exists in several forms, including diffusible and non-diffusible forms. Non-diffusible forms of plasma calcium include that calcium which is bound to proteins in the blood, while the diffusible forms include free ionized and complexed plasma forms of calcium found in blood. Of the different forms of calcium found in the plasma, it is free ionized calcium that is the physiologically active form in plasma.

In general, average total plasma calcium values in humans vary from between 9 and 11 mg/100 ml of plasma, with an average of 46% of this calcium being bound to proteins, slightly more being free and ionized, and the remaining amount of calcium being diffusible but complexed. Persons suffering from hypercalcemia generally possess elevated levels of free and ionized calcium in their plasma.

The severity of the hypercalcemia condition encountered in a patient is thought to be directly related to the level of excess ionized calcium present in the blood. Even so, in the present inventive methods, it is envisioned that the active compounds of the present invention will be effective in treating hypercalcemia, regardless of the severity of the condition encountered.

It is additionally noted, that well trained medical physicians may also wish to vary administration of the active compounds of the present invention, as needed or as desired to treat a patient, with or without other antihypercalcemic compositions and/or other compounds, to produce a desired and advantageous effect.

For example, in actual application, the active compounds encompassed herein may be given alone or in combination with other drugs. There are theoretical advantages to using the active compounds with chemotherapeutic agents, steroids, hormonal manipulation, and/or immunotherapy in the present inventive methods. Chemotherapeutic agents would be toxic to malignant cells causing hypercalcemia, helping to cause a decrease in the amount of osteoclast activating factors which are released, and therefore, active compounds herein encompassed would have less bone resorption activity to antagonize. Some steroids, at high enough doses, can have similar effects in some malignancies. Additionally, it is noted that low dose steroids are given to some patients to prevent hypoadrenalcorticolism, which can be a side effect of suramin (one of the active compounds herein encompassed). Hormonal manipulation is another strategy which can be used to affect the growth of some tumors, such as prostate cancer, in order to decrease the bone resorption activity as described with more traditional chemotherapy, and thus, such agents can be beneficial to administer in conjunction with the active compounds herein taught. Immunotherapy, the use of agents to stimulate the body's immune system, is another approach to combine antitumor treatment with the bone resorbing antagonism of the active compounds herein encompassed.

When the active compounds of the present invention are administered to treat hypercalcemia, it is possible to lower levels of free ionized calcium found in the blood, to normal levels. By lowering such levels of calcium, it is thought possible to additionally aid in the prevention of conditions or events, to which hypercalcemia can lead. Such conditions or events, to which hypercalcemia can lead. Such conditions or events would include arrhythmias as well as altered renal and mental functioning, among others. Additionally, of course, side effects directly associated with hypercalcemia would also be avoided.

The compounds of the present invention, and especially suramin, are thought most advantageous to utilize in the treatment of hypercalcemia due to their long half lives in human plasma. In this regard, it is noted that suramin's half life is approximately 45-55 days in human plasma. As such, it should be clear that upon administration or attainment of an effective plasma level of suramin in a patient for treating hypercalcemia, such levels can be easily maintained for from 6-8 weeks easily without readministering suramin. Thereafter, when suramin levels in the patients' plasma drop below effective levels, additional suramin can be administered, preferably in a brief cycle to again produce effective suramin levels. It should be recognized that the compounds of the present invention possess a clear advantage over previous agents utilized to treat hypercalcemia, since the active compounds of the present invention possess long half lives in plasma, which allows for prolonged periods of time between treatments therewith, once an effective plasma level of one of the active compounds has been obtained.

Methods for administering the active compounds of the present invention preferably include administration by intravenous bolus dose and slow intravenous infusion. Whichever of these methods is utilized, it is thought preferable that plasma levels of greater than about 350 mcg/ml should not be surpassed. Most preferably, it is thought that plasma levels of the compounds above about 300 mcg/ml should not be surpassed. In order that plasma levels always stay below these levels, it is thought that slow intravenous infusion of the compounds is most advantageous in the present invention, with an infusion of about 50 to 5000 mg/m$^2$/day, preferably 100 to 350 mg/m$^2$/day being thought sufficient for ultimately achieving effective plasma levels of the compounds in a period of from about 1 to 7 days for a patient having 1.7 m$^2$ of surface area.

If one practicing the present invention desires to administer compounds of the present invention in intravenous bolus doses, it is thought that the bolus doses should contain about 500 to 5000 mg of the active compounds, preferably 1000 to 2500 mg, of the active compounds. Such bolus doses, it is thought, could be administered from 1 to 4 times per day depending on the weight as well as other characteristics of the patient, until effective levels of the active compounds are obtained.

Whether one skilled in the art utilizes intravenous bolus dosing or intravenous infusion to administer the active compounds of the present invention, it is thought most advantageous that determination of plasma concentration levels of the compounds be obtained 1 to 7 times per week during administration of the compounds, so that the treating physician knows when an effective level of the compounds has been achieved, and alternatively so that amounts greater than about 300 to 350 mcg/ml of plasma are not achieved, and thereby possible unwanted toxic side effects avoided. It should be noted that Stein et al, in U.S. patent application No. 07/321,055, filed Mar. 9, 1989, fully disclose a method of achieving suramin serum (plasma) levels of from about 50 to 300 mcg/ml in a patient without producing unwanted side effects. Such a method is considered advantageous to utilize in the present invention, when treatment of hypercalcemia with the present invention's active compounds is desired.

While suramin and its active analogues herein taught are all effective in the present inventive methods, it is realized that certain of the active compounds, and/or salts thereof, may be most preferable to utilize in the present invention. When determining which active compounds encompassed herein are most preferred to utilize in the present invention, one should examine the compounds' plasma half lives, their toxicity and their ability to block the binding of a wide range of tumor growth factors to their respective receptors. The ability of the active compounds to block tumor growth factors, at their respective receptors, is thought key to effectiveness in the present inventive methods, since many of these tumor growth factors stimulate bone resorption, which in turn increases plasma calcium levels.

In the instance of suramin, the compound possesses relatively low toxicity (when used at the levels herein taught), it has a long plasma half life, and has been shown to block a range of tumor growth factors, including PDGF, TGF-B, EGF, to their cell surface receptors. Based on these considerations and the experimental testing results contained herein, it is thought that suramin is one of the most preferable compounds to utilize in the present invention of those encompassed hereby.

In order to evidence the effectiveness of the compounds encompassed hereby in the present inventive methods, certain in vitro and in vivo testing was performed. The materials and procedures utilized in such testing, as well as results obtained, are as follows.

MATERIALS AND METHODS

Chemicals and Reagents

Dulbecco's modified eagle media (DMEM) was obtained from Biofluids (Catalog No. 104). Serumless media (Neuman and Tytell) was obtained from Gibco (Catalog No. 320-1630 AJ). Glutamine was obtained from Biofluids (Catalog No. 300). Horse serum obtained from Biofluids, Inc. (lot number 18089). Antibiotics were obtained from Biofluids (List No. 329). HEPES was obtained from Biofluids (Catalog No. 305). Heparin was obtained from Organon (1000 units/cc). Human para-thyroid hormone (PTH) (1-34) (Catalog No. 6101; Peninsular Laboratories Incorporated) was stored in 100 $\mu$l aliquots of 100 micrograms per cc. 200 $\mu$l aliquots of Human PTH-related protein (PTH-RP) (1-34) (Catalog No. 6151; Peninsular Laboratories Incorporated) were lyophilized and stored. It was initially dissolved in 50 mM acetic acid, so that the final concentration would be $1.24 \times 10^{-5}$ Molar. Suramin (Mobay Chemical Corporations, New York, NY) was stored in 1 cc aliquots of 10 milligrams per cc. Above factors were stored at $-20$ degrees centigrade.

Bone Resorption Assay

Three to six day old mice (In:GP(s)) were obtained from the small animal section of the Veterinarian Resources Branch of the National Institutes of Health. Calvaria were harvested and washed in 500 cc of Hank's Balanced Salt solution without calcium or magnesium (Catalog No. 320, Biofluids) with a stirring bar for one to one and a half hours. The calvaria were placed in 2cc of study media in 16 × 125 mm STYRENE tissue culture tubes (Catalog No. R605, Elkay Products, Inc.). Study media was made by mixing equal volumes of Media A and Media B and then adding the appropriate growth factors. Media A consisted of Serumless Media with glutamine (1.47 mM) and HEPES (9.8 mM). Media B consisted of DMEM with horse serum (15%), glutamine (1.99 mM), Penicillin (99.57 Units per cc), streptomycin (99.57 $\mu$g per cc), fungizone (0.249 $\mu$ per cc) and heparin (3000 units per cc). The culture tubes were placed in a Cel-Gro Tissue Culture Rotator (Lab-Line Instruments, Inc.) and aerated daily with a mixture of 5% Co2, 45% N2, 50% O2 (MG Industries). The calcium in the media was determined after three days with an ABBOTT Bichromatic Analyzer 100.

EXAMPLE 1

Utilizing appropriate materials in the above described bone resorption assay procedure, the following results were obtained and are shown in FIG. 1A, wherein:
Empty bar: media alone (6.86 +/− 1.23 mg/dl (mean +/− SEM); n=3).
Solid bar: media with calvaria added (9.88 +/− 1.49 mg/dl; n=6).
Striped bar: media with calvaria added plus suramin (200 mcg/ml) (7.05 +/− 0.32 mg/dl; n=6).
The differences in these groups were statistically significant (media alone vs. media with calvaria, P=0.12; media with calvaria vs. media with calvaria plus suramin, P=0.0002).

EXAMPLE 2

Utilizing appropriate materials in the above described bone resorption assay procedure, the following results were obtained and are shown in FIG. 1B, wherein:
Empty bar: media with calvaria added (8.26 +/−0.86 mg/dl; n=6).
Solid bar: media with calvaria added plus Parathyroid Hormone (PTH) (200 ng/ml) (9.89 +/− 0.88 mg/dl; n=6).
Striped bar: media with calvaria added plus PTH plus suramin (200 mcg/ml) (8.33 +/− 0.57 mg/dl; n=6).
The differences in these groups were statistically significant (media with calvaria vs. media with calvaria plus PTH, P=0.0086; media with calvaria plus PTH vs. media with calvaria plus PTH plus suramin, P=0.0045).

EXAMPLE 3

Utilizing appropriate materials from the above-described bone resorption assay procedure, the following results were obtained and are shown in FIG. 1C, wherein:
Empty Bar: media with calvaria added (9.1 +/− 0.46 mg/dl; n=6).
Solid Bar: media with calvaria added plus Parathyroid Hormone - related protein (PTH-rp) (200 ng/ml) (11.3 +/− 0.34 mg/dl; n=10).
Striped bar: media with calvaria added plus PTH-rp plus suramin (200 mcg/ml) (7.26 +/− 0.18 mg/dl; n=10).
The differences in these groups were statistically significant (media with calvaria vs. media with calvaria plus PTH-rp, P=0.0015; media with calvaria plus PTH-rp vs. media with calvaria plus PTH-rp plus suramin, P=0.0001).

Based on results obtained in the above Examples 1-3, it is determined that suramin possesses properties which allow it to inhibit bone resorption, and thus also allow it to lower plasma levels of calcium, including calcium in a diffusible free ionized form.

EXAMPLE 4

As reported by Stein et al in J. Clinical Oncology, Vol. 7, pp. 499-508 (1989), a patient having symptomatic hypercalcemia, characterized by anorexia, weight loss, and lethargy and having calcium levels of 14 to 15 mg/dL, was becoming refractory to treatment with calcitonin, however, after initiation of suramin treatment, the patient became normocalcemic within about two weeks, and calcitonin was withdrawn. The patient remained normocalcemic for three months after treatment with suramin. When the suramin treatment was initiated, the patient was administered suramin at a level of 350 mg/m$^2$/d via continuous infusion for about two weeks, so that a plasma suramin level of 250 to 300 mcg/ml could be obtained.

Based upon the results contained in Experiment 4, it is fully envisioned that suramin and each of the active analogues herein taught, possess utility in the treatment of hypercalcemia in patients afflicted therewith, and that such treatment effects are long lived.

PHARMACEUTICAL COMPOSITIONS

When administering suramin or the active analogues thereof, in the methods of the present invention, it is envisioned that certain pharmaceutical compositions may be employed. Such compositions should be capable of administration by the desired route, i.e., by an intramuscular, subcutaneous or intravenous route. Moreover, the pharmaceutical compositions should contain suramin or an active analogue thereof in such concentration that infusion or bolus administration of a required amount of the active compound is not unduly difficult to manage. For example, it is thought that when the active compounds of the present invention are administered as a solution, the total amount of solution administered per 24 hr period should not be greater than about 200 ml to about 1,000 ml.

An appropriate intravenous solution (for infusion) for administering suramin or an active analogue thereof in the method of the present invention, could include, for example, 400 mg to 4.0 gm of the chosen active compound in 250 ml sterile water for injection USP or other appropriate pharmaceutical carrier. With such a solution, there could be infused into a patient from about 16 to about 160 mg/hr of the active compound utilized to treat hypercalcemia.

In one preferred embodiment of the present invention, it is thought that one can administer the active compounds in an appropriate intravenous carrier, with the aid of a portable pump metering the administration of the active compound over periods of about 24 hours. The use of metering pumps in practicing the methods of the present invention should be readily understood by those skilled in the art.

Alternatively, if bolus doses are contemplated, volumes of less than about 250 to 150 ml's are thought preferred. Such bolus doses would, of course, include an appropriate amount of an active compound herein taught (e.g., 500 to 5000 mg) depending on the volume to be injected.

Active ingredients of the present invention administered in such a manner as provided with the pharmaceutical compositions discussed herein, will generally preclude producing elevated plasma concentration levels of the active agent (i.e., greater than about 300 to 350 mcg/ml) in a patient, unless or until a patient's body has been fully loaded with the active compound, over a period of days, so that a concentration equilibrium level exists between the amount of the active compound contained in said patient's plasma and said patient's tissues or organs, etc., whereby said plasma concentration level of the active compound is already elevated to about 300–350 mcg/ml. In any event, periodic, quantitative determinations of the active compounds concentration level, as provided for herein, should allow one skilled in the art to keep peak blood levels of the active ingredients to about not greater than about 300 to 350 mcg/ml, even when the largest doses of the active compounds provided for herein are administered in pharmaceutical compositions as provided herein.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for the treatment of hypercalcemia in a patient in need of such treatment, the method comprising:

administering by injection t the patient an effective amount of suramin, or a pharmaceutically acceptable salt thereof, for lowering the patient's plasma calcium level.

2. The method of claim 1, wherein said suramin or the pharmaceutically acceptable salt thereof is administered by bolus injection or by intravenous infusion.

3. The method of claim 1, wherein a plasma level of said suramin or the pharmaceutically acceptable salt thereof is achieved of between about 50 to about 350 mcg/ml of plasma in the patient.

* * * * *